United States Patent [19]

Fowles et al.

[11] Patent Number: 5,429,614

[45] Date of Patent: Jul. 4, 1995

[54] DRUG DELIVERY SYSTEM

[75] Inventors: Thomas A. Fowles, McHenry; Richard A. Rollins, Mundelein; Mark A. Hoekwater, Vernon Hills, all of Ill.

[73] Assignee: Baxter International Inc., Deerfield, Ill.

[21] Appl. No.: 86,434

[22] Filed: Jun. 30, 1993

[51] Int. Cl.[6] .................. A61M 5/24; A61M 5/28
[52] U.S. Cl. .................. 604/201; 604/85; 604/88; 604/415
[58] Field of Search .................. 604/56, 82–92, 604/411–414, 416, 201, 205, 206, 220; 206/219, 222; 141/329, 330

[56] References Cited

U.S. PATENT DOCUMENTS

| | | | |
|---|---|---|---|
| 4,576,211 | 3/1986 | Valentini et al. | 141/329 |
| 4,759,756 | 7/1988 | Forman et al. | 604/413 |
| 4,804,366 | 2/1989 | Zdeb et al. | . |
| 4,850,978 | 7/1989 | Dudar et al. | 604/201 |
| 4,982,769 | 1/1991 | Fournier et al. | 141/98 |
| 5,088,996 | 2/1992 | Kopfer et al. | 604/415 |
| 5,116,316 | 5/1992 | Sertic et al. | 604/83 |
| 5,167,642 | 12/1992 | Fowles | 604/263 |
| 5,171,214 | 12/1992 | Kolber et al. | 604/82 |
| 5,324,256 | 6/1994 | Lynn et al. | 604/49 |
| 5,342,346 | 8/1994 | Honda et al. | 604/413 |

*Primary Examiner*—C. Fred Rosenbaum
*Assistant Examiner*—V. Alexander
*Attorney, Agent, or Firm*—Mark J. Buonaiuto; Paul E. Schaafsma; Paul C. Flattery

[57] ABSTRACT

An improved drug delivery system and method for reconstituting drugs are provided. The system allows the delivery of a medicament from a drug vial (40) directly into an intravenous line to a patient. The system provides a method and an apparatus that insures that the drug vial (40) is properly pierced and the vial (40) is locked into an activated position when it is desired to use the same. To this end, a vial retaining member (50) for coupling the vial (40) to a cartridge (12) including a cannula (22) is provided. The retaining member (50) includes a cannula centering member extending from an end thereof.

25 Claims, 3 Drawing Sheets

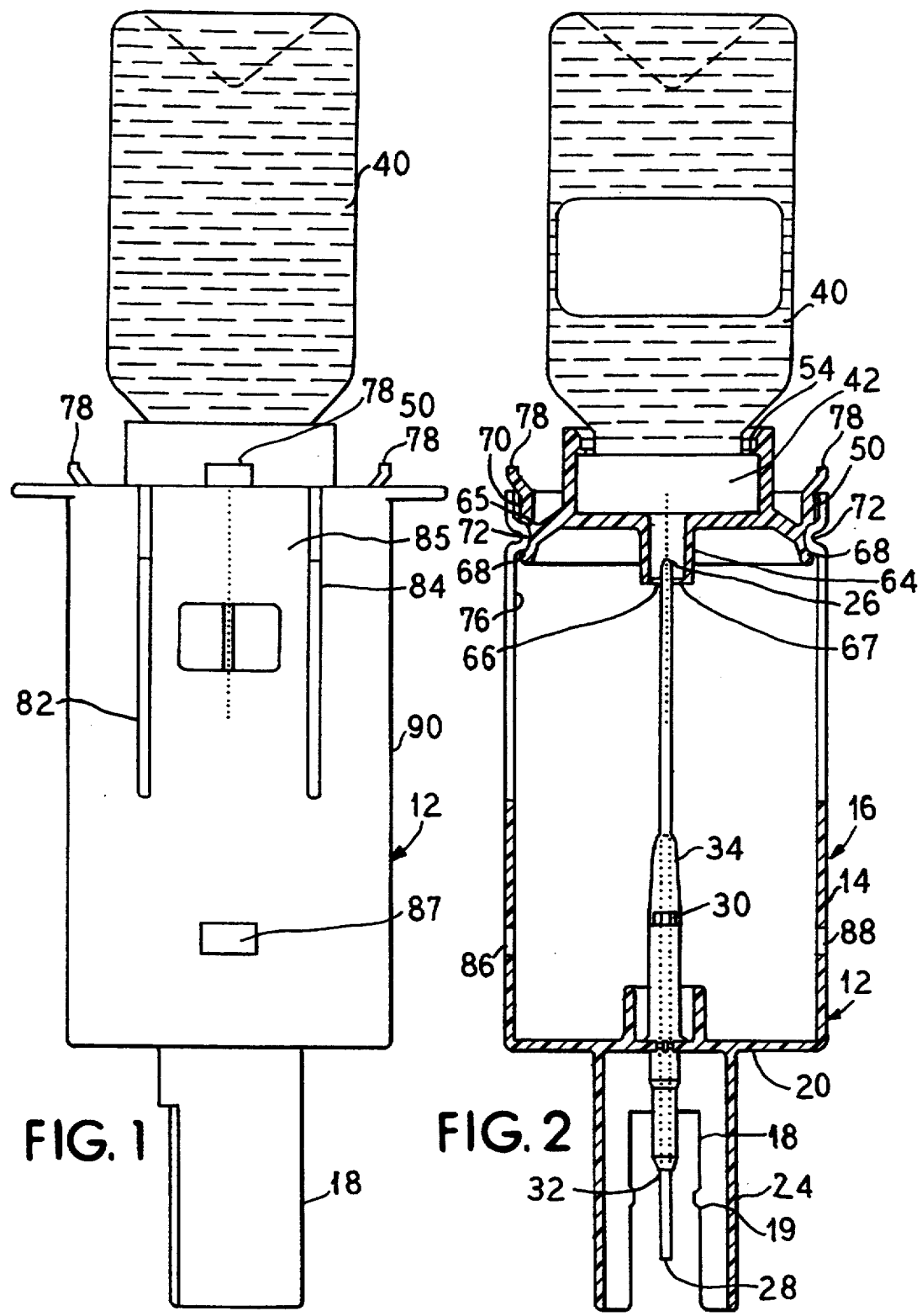

DRUG DELIVERY SYSTEM

BACKGROUND OF THE INVENTION

The present invention relates generally to the delivery of a beneficial agent to a patient or into a system for later delivery to a patient. More specifically, the present invention relates to drug delivery systems.

For many applications, drugs are mixed with a diluent before being delivered, for example, intravenously, to a patient. The diluent can be, for example, a dextrose solution, a saline solution, or even water. To this end, many such drugs are supplied in powder form and packaged in glass vials or ampules. Other drugs, such as some chemotherapy drugs, are packaged in glass vials or ampules in a liquid state.

Powdered drugs can be reconstituted by utilizing a syringe to inject liquid into a vial for mixing; the syringe eventually withdrawing the mixed solution from the vial. When a drug must be diluted before delivery to the patient, the drug is often injected into a container of diluent after it is reconstituted; the container can be connected to an administration set for delivery to the patient.

Drugs may be packaged separately from the diluent for various reasons. One of the more important reasons is that many drugs do not retain their chemical and physical stability when mixed with a diluent and thus, cannot be stored for any substantial period of time. Also, drugs are often packaged separately from the diluent because many companies that manufacture drugs are not engaged in the business of providing medical fluids and containers for intravenous delivery and vice versa.

Therefore, a doctor or nurse, a pharmacist, or other medical personnel must mix the drug and diluent. This presents a number of problems. The reconstitution procedure is time consuming and requires aseptic technique. The operator must provide the proper diluent in a syringe before beginning. Often the powdered drug is "caked" at the bottom of the vial. Thus, when liquid is injected into the vial from a syringe, the surface area of contact between the liquid and the powdered drug may be quite small. Initially, this may make the mixing procedure even more time consuming.

Because of the limited vial volume, increasing the drug concentration in the diluent makes it harder to complete the reconstitution process. The operator may attempt to solve this problem by repeatedly injecting solution into the vial, mixing and withdrawing the solution. This attempt to solve the problem makes additional injections and movement of the syringe necessary, increasing the likelihood of contamination. Also, it is sometimes difficult to remove all of the drug and/or liquid from the vial, thus increasing the time required to perform the reconstitution procedure.

The reconstitution procedure should be performed under preferably sterile conditions. This requirement requires the operator to be more cautious, thereby consuming more time. Additionally, sterile conditions are often hard to maintain. In some instances, a laminar flow hood may be required in which the reconstitution procedure is performed. A further concern is that some drugs, such as chemotherapy drugs, are toxic. Exposure of the operator to the drugs during reconstitution can be dangerous, especially if the operator works with such drugs on a daily basis and is repeatedly exposed to them.

After a drug is reconstituted and withdrawn into a syringe barrel, the drug can, in some instances, be immediately injected into the patient. More typically, however, the reconstituted drug is injected from the syringe into a larger container of solution for connection to an intravenous administration set. A larger container of solution may be necessary because often the reconstituted drug in the syringe is at such a concentration as to cause local toxicity in the veins of a patient near the injection site where the needle pierces the skin. This can create severe vein irritation which can be harmful.

Additionally, even though the proper dose of medication may be in the syringe, immediate injection into the patient's blood stream can create a condition of systemic toxicity wherein the level of drug concentration in the patient's entire blood stream is dangerously high. Yet another reason for not making an injection from the syringe directly into the patient is that such injection creates an additional injection site into the patient; this can be painful to the patient and provides another opportunity for infection.

For these reasons, the reconstituted drug is more typically injected into a diluent container.

There are a variety of examples of drug delivery systems that can be used to deliver drugs to a patient and/or reconstitute a drug. An example of such a system is disclosed in U.S. Pat. No. 4,850,978. The system includes a cartridge for introducing a beneficial agent into a fluid conduit for delivery of the agent to a patient. The cartridge includes a rigid hollow tube and an agent-containing chamber slidably mounted at least partially within the hollow tube. In a first, pre-use position, the chamber extends farther from the hollow tube than it does in a second position. A cannula is mounted to the hollow tube extending opposite the chamber. When the chamber is in the second position, the cannula pierces the closure means creating a fluid flow path.

U.S. Pat. No. 4,804,366 also discloses a drug delivery system including an adaptor having an improved flow path means providing both an inlet and an outlet to the agent-containing chamber of a cartridge. The cartridge and adaptor permit a single opening through the injection sites at opposite ends of the flow path means, while still permitting simultaneous flow both into and out of the chamber. An adaptor in the cartridge is provided, including a rigid cannula with an inlet and an outlet and a shell substantially coaxial with and spaced from the cannula intermediate of the cannula inlet and the cannula outlet, so that the shell of the cannula defines a channel therebetween. Both the cannula inlet and the cannula outlet are adaptable to form a single piercing opening in a resilient injection site associated with the receptacle of the delivery system. Both the channel outlet and cannula inlet are adapted to form a single piercing opening in a resilient injection site associated with the cartridge.

The drug vials and specifically the stoppers may have a variety of different shapes and constructions depending on the composition contained therein. For example, lyophilized and non-lyophilized drug vials have different stopper types. The lyophilized stopper typically has a different geometry than a non-lyophilized stopper. Due to the construction of the lyophilized stopper, certain issues may be raised. For example, the geometry of the lyophilized stopper will require the cannula to accurately pierce the center of the lyophilized stopper. Missing the stopper target, or center of the lyophilized stopper, and entering the vial on an angle can result in an occluded vial inlet flow path and thereby a failure of the drug delivery device to deliver the dose (stop flow).

Another issue with respect to drug vial stoppers is the inconsistency or lack of lubrication. In a drug delivery device such as those set forth above, insufficient stopper lubrication can result in the stopper resisting cannula penetration. Once the user releases the pressure used to pierce the stopper, the vial can "spring back" thereby preventing total cannula penetration. The result can be an occluded flow path, i.e., stop flow.

SUMMARY OF THE INVENTION

The present invention provides an improved drug delivery system. The system allows the delivery of a medicament from a drug vial directly into an intravenous line to a patient. The system provides a method that insures that the drug vial is properly pierced and the vial is locked into an activated position when it is desired to use the same.

To this end, in an embodiment, a cartridge for introducing a beneficial agent into a fluid conduit for delivery of the beneficial agent to a patient is provided. The cartridge includes a hollow tube. A vial having a beneficial agent therein is coupled by a retaining member to a first end of the hollow tube, the vial being slidably mounted at least partially within the hollow tube from a first position to a second position, such that in the first position, the vial extends a greater distance from the hollow tube than in the second position. A cannula is mounted within the hollow tube. The retaining member includes means for allowing the retaining member and vial to move from the first position to the second position and means for centering the cannula so that it pierces a center of a stopper that closes the vial.

In an embodiment, the means for centering the cannula is an elongated member, having an aperture, the elongated member extending from the retaining member toward the cannula and away from the vial. In a further embodiment, the aperture is defined by a flexible skirt.

In an embodiment, the retaining member includes at least one locking tab.

In an embodiment, the retaining member includes an upper portion and a lower portion, the upper portion having means for retaining at least a part of the vial therein and the lower portion includes means for centering the cannula.

In an embodiment, the retaining member defines an interior area for receiving a portion of the vial and includes means for securing the portion of the vial within the interior area.

In an embodiment, the means for securing includes a flange circumscribing at least a portion of the interior area.

In an embodiment, the hollow tube includes at least one inwardly extending flange that is received by a groove in the retaining member.

In an embodiment, the hollow tube includes at least one aperture for receiving a portion of the retaining member and securing the retaining member in place in the second position.

In an embodiment, the hollow tube includes means for allowing walls of the hollow tube to be biased outwardly as the retaining member moves from the first to the second position. In a preferred embodiment, the means includes longitudinal slots.

The present invention also provides a drug delivery device. The device includes a cartridge body including an upper portion defining a vial receiving area and terminating in a wall, the cartridge body including a cannula extending from the wall. A vial including a beneficial agent is coupled to the cartridge body by a retaining member that maintains the vial in an inactivated position and allows the vial to move to an activated position wherein one end of the cannula penetrates into the vial. The retaining member includes an upper portion and a lower portion, the upper portion including an area for receiving at least a portion of the vial and the lower portion including a centering member extending therefrom for centering the cannula, the centering member includes an aperture for receiving the cannula.

Additionally, the present invention provides a drug vial retaining member for coupling a vial to a drug delivery cartridge body that includes a cannula disposed therein. The retaining member includes a body having means for removably coupling the retaining member to an end of the cartridge body, an interior for receiving at least a part of the drug vial, and extending from a lower portion thereof a centering member that includes an aperture that is defined by a flexible skirt.

Further, the present invention provides a method for reconstituting a drug comprising: providing a cartridge body that includes a cannula; coupling a retaining member having a first part and a second part to an end of the cartridge body; securing the vial including the drug to the end of the cartridge body by inserting at least a portion of the vial into an interior of the retaining member; and causing the cannula, prior to piercing the vial, to be received in a centering member that extends from an end of the retaining member.

It is an advantage of the present invention to provide an improved drug delivery system.

A further advantage of the present invention is that it provides a drug delivery system that insures that the vial stopper is properly pierced by the cannula of a drug delivery system.

Moreover, an advantage of the present invention is that it provides a drug delivery system that can be used with lyophilized agents.

Another advantage of the present invention is that it provides a system wherein the vial is locked down in position once the system is activated preventing the vial from springing back.

Still further, an advantage of the present invention is that it provides a drug delivery system that prevents the occluding of the flow path, that can result in a stop flow, even when used with a lyophilized drug vial.

Additional features and advantages of the present invention are described in, and will be apparent from, the detailed description of the presently preferred embodiments and from the drawings.

BRIEF DESCRIPTION OF THE DRAWINGS

FIG. 1 illustrates a perspective view of an embodiment of the drug delivery device of the present invention in a first, inactivated position.

FIG. 2 illustrates a cross-sectional perspective view of the drug delivery device of FIG. 1.

DETAILED DESCRIPTION OF THE PRESENTLY PREFERRED EMBODIMENTS

Figure 3:
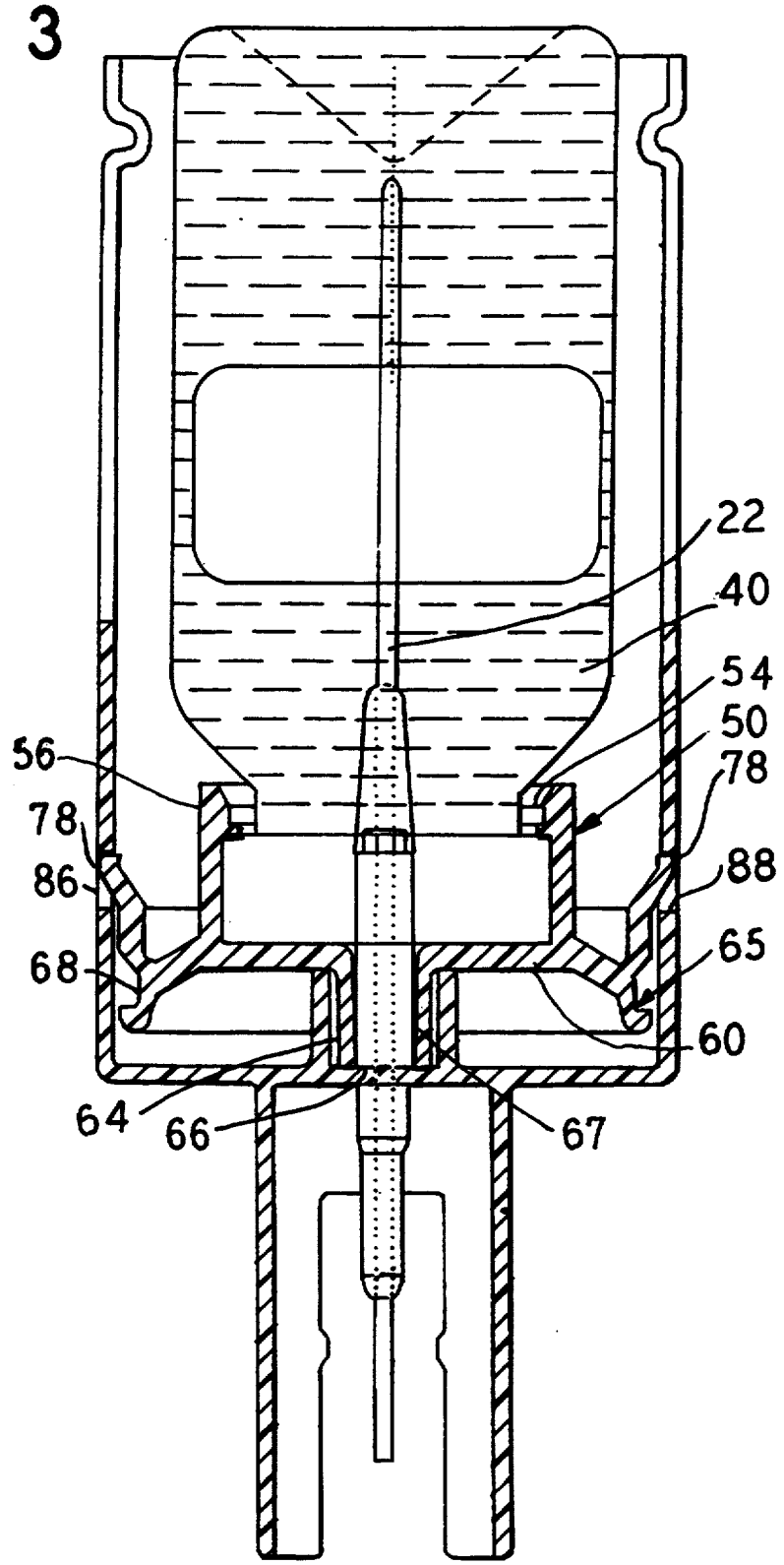
FIG. 3 illustrates a cross-sectional perspective view of the drug delivery device of FIG. 2 in a second activated position.

The present invention provides an improved drug delivery device. The drug delivery device provides means for centering the cannula of a drug delivery device so that it properly pierces the stopper of a vial. Furthermore, the device of the present invention insures that the vial when it is in a second activated position is locked in place.

Referring now to FIGS. 1 and 2, there is illustrated an in-line device, or cartridge, that is to be coupled to an IV set. The cartridge, in some respects, is similar to that disclosed in U.S. Pat. No. 4,804,366, the disclosure of which is incorporated herein by reference. Briefly, the cartridge 12 includes an adaptor 14 having a substantially rigid hollow cylinder or tube 16 and a keyway wall 18, with the keyway wall 18 being part of the tube 16. The keyway wall 18 includes snaps 19 which assist in containing the cartridge 12 on the IV set. A plate 20 is mounted across the tube 14 and defines the starting point for the keyway wall 18.

A cannula 22 extends through the plate 20. A generally cylindrical shell 24 extends from both sides of the plate 20. The hollow tube 16, the plate 20, the keyway wall 18, and the shell 24 may all be formed as a single piece of the same material, such as a plastic.

The shell 24 is spaced apart from the cannula 22 with the shell 24 encompassing the cannula 22, but being shorter than either end of the cannula 22. The cannula 22 includes an inlet 26 and an outlet 28. The inlet 26 can be pointed to facilitate piercing. In a preferred embodiment, the inlet 26 of the cannula has a conical structure such as that disclosed in U.S. Pat. No. 5,226,902, the disclosure of which is hereby incorporated by reference. The outlet 28 can also be pointed, but can be, in an embodiment such as that depicted in FIG. 2, blunt.

Likewise, if desired, the outlet can be covered by a sheath (not shown). In this regard, reference is made to U.S. Pat. No. 5,167,642, the disclosure of which is incorporated herein by reference.

The shell 24 is intermediate of the cannula inlet 26 and the cannula outlet 28, respectively. The cannula 22 and the shell 24 define a channel 30 therebetween. In a preferred embodiment, the periphery of the cannula 22 is circular along its length. In an embodiment, the internal surface of the shell 24 can also be circular along its length.

The channel 30 includes a channel inlet 32 defined between the shell 24 and the cannula 22 short of the cannula outlet 28. Similarly, the channel 30 includes a channel outlet 34 defined by the shell 24 and the cannula 22 short of the cannula inlet 26.

The shell can be secured to the cannula as disclosed in U.S. patent application Ser. No. 08/085,999 filed Jun. 30, 1993, entitled: "BI-DIRECTIONAL RECONSTITUTION INTRODUCER" being filed herewith, the disclosure of which is incorporated herein by reference.

However, the shell and cannula construction can be such as that shown in U.S. Pat. No. 4,804,366 wherein a plastic cannula holder is secured to the cannula. The cannula holder grips the cannula. Extension means extend between the cannula holder and the shell, across the channel, thereby securing the cannula relative to the shell. The cannula is secured to the shell while still maintaining an open flow path through the cannula inlet, the channel, and the channel outlet. Thus, a very small flow path is created outside a single cannula, with precision.

As discussed in more detail below, the cartridge 12 further includes, or is coupled to, a tubular chamber or vial 40 containing a beneficial agent, such as a dry, powdered drug, although the agent could be liquid. In an embodiment, the tubular chamber is a glass vial 40 having a pierceable stopper 42 or other closure means that closes the glass vial 40.

The shell 24, along with the channel outlet 34 and the cannula inlet 26, are designed to pierce the pierceable stopper 42 or other injection site/closure means to enter the vial 40 having the beneficial agent therein. Similarly, the shell 24, along with the defined channel inlet 32, together with the cannula outlet 28 are designed to pierce the injection site in a receptacle.

The pierceable stopper 42 is mounted within the mouth of the vial 40. The pierceable stopper 42 can be secured within the vial 40 by means of a metal band about the periphery of the mouth and the rubber stopper, in a known manner for securing a stopper in a standard drug vial. The vial 40, as discussed below, is slidably mounted within the rigid cylinder, such that the rubber stopper faces the plate 20. In place of the pierceable stopper 42, other pierceable closure means can be provided.

To couple the vial 40 to an end of the tube 16, pursuant to the present invention, a retaining member 50 that, as discussed in detail below, properly centers the vial and locks it in place in an activated position is provided. Pursuant to the present invention, the retaining member 50 allows the vial 40 to be coupled to the tube 16 in a first inactivated position, illustrated in FIGS. 1 and 2. As discussed in more detail below, when it is desired to access the drug or beneficial agent contained within the vial 40, the retaining member 50 allows the vial 40 to be moved into a second activated position, illustrated in FIG. 3, where it is locked in place.

Figure 4:
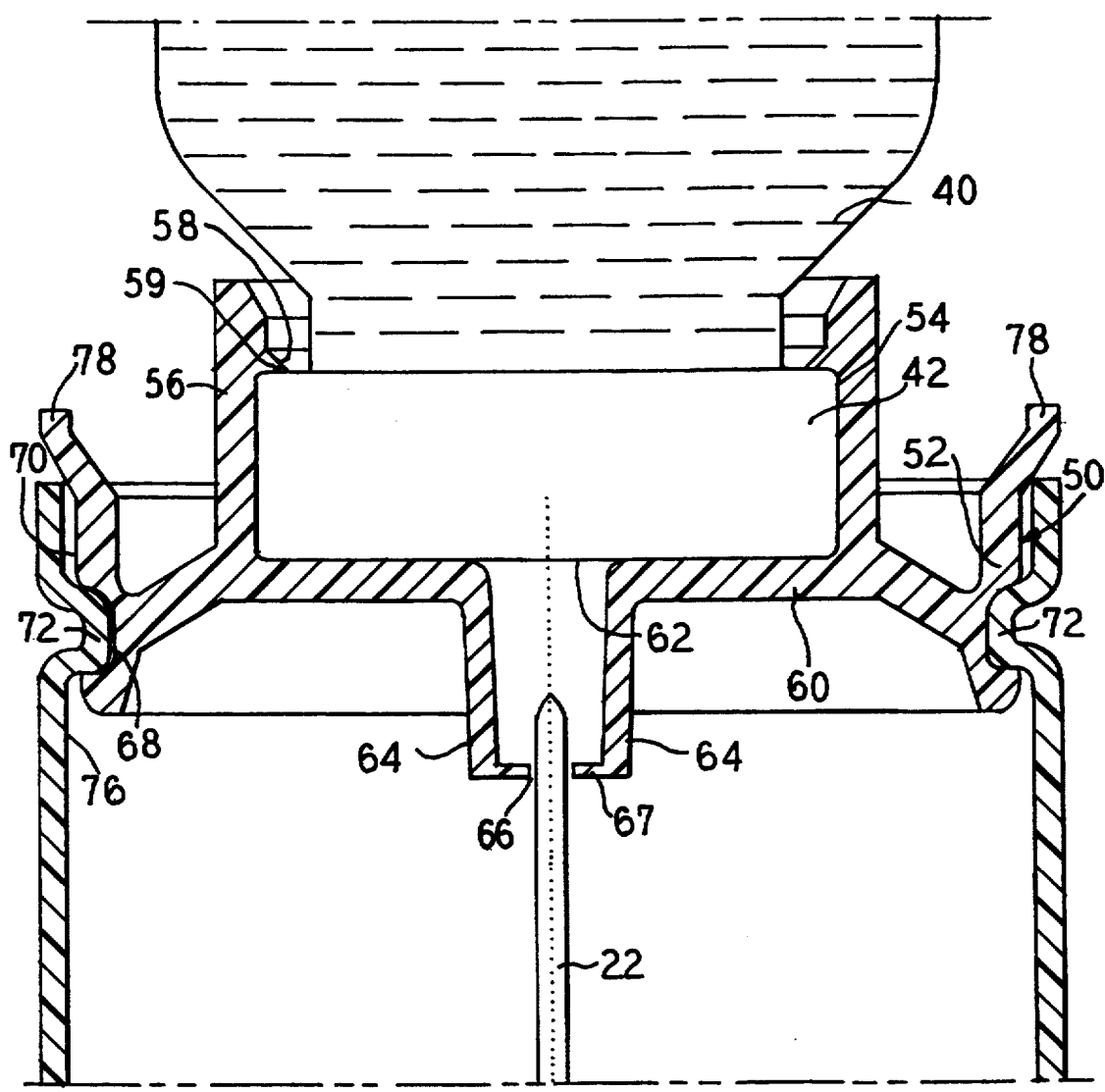
FIG. 4 illustrates a cross-sectional enlarged view of the vial retaining device of the present invention.

Referring now to FIGS. 2–4, the retaining member 50 includes a body 52 having a vial cap receiving area 54 defined by walls 56. The area 54 is designed to receive and secure therein at least the cap of the vial 40. To this end, the walls 56 include an inwardly extending flange 58 that circumscribes the inner walls. As illustrated, the flange 58 allows a vial cap or stopper 42 to be secured within the area 54. To this end, the flange 58 includes a bevelled portion 59 that allows the cap to snap into the area. The vial cap is thereby securely received within the body 52 of the retaining member 50 securing the vial 40 in place.

The walls 56 terminate at a floor 60 of the body 52. The floor 60 is designed to support, at least in part, the vial 40 when it is received within the area 54. As discussed in more detail infra, the floor 60 includes an aperture 62 that allows the cannula 22 to pierce the vial stopper 42.

Extending from the floor 60, in a direction opposite the vial 40 is a centering member 64. The centering member 64, in the preferred embodiment illustrated, is an elongated member that terminates in an aperture 66. In the preferred embodiment illustrated, the aperture 66 is defined by a flexible skirt 67, preferably constructed from a flexible plastic. The flexible skirt 67 creates the aperture 66 having a size that is slightly greater than the outer circumference of the cannula 22.

As illustrated in FIGS. 2 and 3, the centering member 64 allows the cannula 22 and the shell 24 to pierce the vial stopper 42. However, the centering member 64 prevents the cannula 22 and the shell 24 from piercing the vial stopper 42 in any manner that is not directly within the center of the vial stopper 42 and substantially perpendicular to a plane across the top of the vial stopper 42. This insures that the vial stopper 42 is always pierced directly through the center thereof and not offset. This prevents any occlusion of the cannula 22 or the shell 24 when a lyophilized drug is being reconstituted.

As illustrated in FIG. 3, due to the flexible nature of the skirt 67, it folds back when the vial 40 is moved to the activated position. This allows the shell 24 to also pierce the vial stopper 42. If desired, the centering member 64 need not include the flexible skirt 67.

The body 52 of the retaining member 50 also includes means for removably securing 65 the retaining member 50 to the cartridge 12. This means 65 includes a recessed portion 68 that preferably circumscribes the outer surface 70 of the member 50. This recessed portion 68 is designed to mate with inwardly extending flange members 72 that extend from an inner circumference 76 of the upper part of the hollow tube 16.

In the preferred embodiment illustrated, the hollow tube 16 includes four flange members 72. The four flange members 72 correspond to the locking tabs 78 (three of which are illustrated) extending from the outer surface 70 of the body 52 of the retaining member 50. Of course, more or less than four locking members can be used.

The flange members 72 of the hollow tube 16 insure that the retaining member 50 is properly positioned. To this end, the locking tabs 78 are aligned with the flanges 72, and the retaining member 50 is then snapped into place. This locks the retaining member 50 to the hollow tube 16.

The hollow tube 16 preferably includes slots 82 and 84 that define a movable wall 85 on the hollow tube. The slots 82 and 84 are located along a partial length of the hollow tube 16. In a preferred embodiment, a second set of slots are located on an opposite side of the hollow tube. Therefore, as the vial 40 and the retaining member 50 move from the first position (see FIG. 2) to the second activated position (see FIG. 3), the movable walls of the hollow tube 16 flex outwardly.

It should be noted that a wide variety of means can be used on the hollow tube 16 to allow the retaining member 50 to move from the first to the second position. For example, the slots can be oriented to receive the locking tabs to allow the tabs to move therein.

The slots 82 and 84 terminate at a location above locking apertures 86, 87, and 88. The locking apertures 86, 87, and 88 are designed to receive the locking tabs 78 and lock the vial 40 in the activated position as illustrated in FIG. 3. When the locking tabs 78 are received in the locking apertures 86, 87, and 88, the user is provided with a tactile feeling.

As illustrated in FIG. 1, preferably, the device 10 is shipped with a shrink wrap 90 surrounding the upper portion of the hollow tube 16, retaining member 50, and a portion of the vial 40. The shrink wrap 90 will prevent inadvertent activation of the vial 40 attached thereto. To this end, in part, the shrink wrap 90 will prevent the movable walls 85 from being biased outwardly.

Although the body 52 and the retaining member 50 can be constructed from a variety of materials, preferably, the retaining member 50 is constructed from a rigid plastic.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A cartridge for introducing a beneficial agent into a fluid conduit for delivery of the beneficial agent to a patient, the cartridge comprising:
    a hollow tube;
    a vial having a beneficial agent therein, the vial coupled by a retaining member to a first end of the hollow tube, the vial being slidably mounted at least partially within the hollow tube from a first position to a second position, such that in the first position, the vial extends a greater distance from the hollow tube than in the second position;
    a cannula mounted within the hollow tube;
    means for allowing the retaining member and the vial to move from the first position to the second position; and
    means for centering the cannula so that it pierces a center of a stopper that closes the vial wherein the means for centering is integrally formed with the retaining member and is constructed and arranged to extend into the hollow tube from the first end.

2. The cartridge of claim 1 wherein the means for centering the cannula is an elongated member, having an aperture, the elongated member extending from the retaining member toward the cannula and away from the vial.

3. The cartridge of claim 2 wherein the aperture is defined by a flexible skirt.

4. The cartridge of claim 1 wherein the retaining member includes at least one locking tab.

5. The cartridge of claim 1 wherein the retaining member includes an upper portion and a lower portion, the upper portion having means for retaining at least a part of the vial therein and the lower portion includes the means for centering the cannula.

6. The cartridge of claim 1 wherein the retaining member defines an interior area for receiving a portion of the vial and includes means for securing the portion of the vial within the interior area.

7. The cartridge of claim 6 wherein the means for securing includes a flange circumscribing at least a portion of the interior area.

8. The cartridge of claim 7 wherein the flange includes a beveled portion.

9. The cartridge of claim 1 wherein the hollow tube includes at least one inwardly extending flange that is received by a groove in the retaining member.

10. The cartridge of claim 1 wherein the hollow tube includes at least one aperture for receiving a portion of the retaining member and securing the retaining member in place in the second position.

11. The cartridge of claim 1 wherein the hollow tube includes means for allowing at least portions of the hollow tube to be biased outwardly as the retaining member moves from the first to the second position.

12. A drug delivery device comprising:
    a cartridge body including an upper portion defining a vial receiving area at a first end and terminating in a wall at a second end, the cartridge body including a cannula extending from the wall at the second end toward the first end;

a vial including a beneficial agent; and a retaining member at the first end of the cartridge body coupling the vial to the vial receiving area at the first end of the cartridge body and maintaining the vial in an inactivated, first position and allowing the vial to move to an activated, second position wherein one end of the cannula penetrates into the vial, the retaining member including an upper portion and a lower portion, the upper portion of the retaining member including an area receiving and retaining at least a portion of the vial and the lower portion including a member extending therefrom and integrally formed with the lower portion thereby centering the cannula including an aperture in the member capable of receiving the cannula.

13. The drug delivery device of claim 12 wherein the retaining member includes at least one locking tab.

14. The drug delivery device of claim 12 wherein the area receiving and retaining a portion of the vial includes means for securing the portion of the vial within the interior area.

15. The drug delivery device of claim 12 wherein the cartridge body includes at least one aperture for receiving a portion of the retaining member and securing the retaining member in place in the second position.

16. The drug delivery device of claim 12 wherein the aperture is defined by a flexible skirt.

17. The drug delivery device of claim 12 wherein the cartridge body includes at least one inwardly extending flange that is received by a groove in the retaining member.

18. The drug delivery device of claim 12 wherein the cartridge body includes at least two longitudinal slots that allow portions of the body to move outwardly as the retaining member moves from the first position to the second position.

19. A drug vial retaining member for coupling a vial to a drug delivery cartridge body that includes a cannula disposed therein, the drug vial retainer member comprising:

a body having an upper portion integrally formed with a lower portion with means for removably coupling the body to an end of the cartridge body, an interior for receiving at least a portion of the drug vial in the upper portion of the body, and an elongated centering member that includes an aperture that is defined by a flexible skirt extending from the lower portion of the body capable of receiving the cannula wherein the elongated centering member is integrally formed with the lower portion of the body.

20. The drug vial retaining member of claim 19 wherein the means for removably coupling includes a recessed portion.

21. The drug vial retaining member of claim 19 further comprising:

at least one locking tab that can be biased inwardly.

22. The drug vial retaining member of claim 19 wherein the flexible skirt is constructed from flexible plastic.

23. A method for reconstituting a drug, the method comprising the steps of:

providing a cartridge body that includes a cannula;

coupling a retaining member having a first part integrally formed with a second part to an end of the cartridge body;

securing a vial including the drug to the end of the cartridge body by inserting at least a portion of the vial into an interior of the first part of the retaining member; and causing the cannula prior to piercing the vial to be received in a centering member that extends from the second part of the retaining member and further extends from the end of the cartridge body having the retaining member into the cartridge body.

24. The method of claim 23 wherein the vial is coupled to the retaining member before the retaining member is coupled to the cartridge body.

25. The method of claim 23 further comprising the step of:

causing a flexible skirt that circumscribes an aperture of the centering member to fold back as a portion of the cannula enters the centering member.

* * * * *